US009783788B2

(12) United States Patent
Chen et al.

(10) Patent No.: US 9,783,788 B2
(45) Date of Patent: Oct. 10, 2017

(54) PORCINE PSEUDORABIES VIRUS (PRV)-YF STRAIN AND ITS APPLICATION

(71) Applicants: Zhaoqing Dahuanong Biological Medicine Co., Ltd, Zhaoqing (CN); South China Agricultural University, Guangzhou (CN)

(72) Inventors: Ruiai Chen, Zhaoqing (CN); Hongliang Huang, Zhaoqing (CN); Changbao Ren, Zhaoqing (CN); Xiaoyu Xie, Zhaoqing (CN); Zheng She, Zhaoqing (CN); Xuanzi Zhan, Zhaoqing (CN); Xiaoxiong Deng, Yunfu (CN); Manhua Tang, Yunfu (CN)

(73) Assignees: Zhaoqing Dahuanong Biological Medicine Co., Ltd, Zhaoqing (CN); South China Agricultural University, Guangzhou (CN)

( * ) Notice: Subject to any disclaimer, the term of this patent is extended or adjusted under 35 U.S.C. 154(b) by 0 days.

(21) Appl. No.: 15/011,608

(22) Filed: Jan. 31, 2016

(65) Prior Publication Data

US 2016/0228538 A1 Aug. 11, 2016

(30) Foreign Application Priority Data

Feb. 11, 2015 (CN) .......................... 2015 1 0075712

(51) Int. Cl.

| | |
|---|---|
| ***C12N 7/00*** | (2006.01) |
| ***A61K 39/12*** | (2006.01) |
| *A61K 39/00* | (2006.01) |

(52) U.S. Cl.

CPC ................ *C12N 7/00* (2013.01); *A61K 39/12* (2013.01); *A61K 2039/5252* (2013.01); *C12N 2710/16721* (2013.01); *C12N 2710/16734* (2013.01); *C12N 2710/16763* (2013.01)

(58) Field of Classification Search

None

See application file for complete search history.

(56) References Cited

PUBLICATIONS

GenBank: EF552427.1 . Suid herpesvirus 1 strain GDSH glycoprotein gE (gE) gene, complete cds. May 19, 2007.*

* cited by examiner

*Primary Examiner* — Nianxiang (Nick) Zou

(74) *Attorney, Agent, or Firm* — Wayne & King LLC

(57) ABSTRACT

The present invention relates to the technical field of porcine pseudorabies virus, and more particularly to a porcine pseudorabies virus (PRV)-YF strain, with the preservation No. of CCTCC No. V201502. The present invention also provides an application of the porcine pseudorabies virus (PRV)-YF strain in preparing an inactivated vaccine of the porcine pseudorabies virus, the inactivated vaccine of the porcine pseudorabies virus and a preparation method thereof. It is proved through an immune efficacy evaluating test and a safety test that the inactivated vaccine of the porcine pseudorabies virus has good immune protective efficacy and is safe for weaned piglets, replacement gilts, pregnant sows and the like.

8 Claims, 5 Drawing Sheets

```
┌─────────────────────────────────────────────┐
│  Reviving Vero cells in the liquid nitrogen │
└─────────────────────────────────────────────┘
                      ↓
┌─────────────────────────────────────────────┐
│     Enlarging and cultivating Vero cells    │
└─────────────────────────────────────────────┘
                      ↓
┌─────────────────────────────────────────────────────────┐
│ Inoculating the tonsil and brain tissue, and separating PRV │
└─────────────────────────────────────────────────────────┘
                      ↓
┌──────────────────────────┐  ┌──────────────────────┐  ┌──────────────────────────┐
│ Analyzing TK,gE and gG   │  │ Porcine pseudorabies │  │ Analyzing virulence and  │
│ sequence and their coded │◄─┤ virus (PRV)-YF strain├─►│ antigenic variation      │
│ amino acid sequence      │  │                      │  │                          │
└──────────────────────────┘  └──────────────────────┘  └──────────────────────────┘
                                         ↓
┌─────────────────────────────────────────────────────────────────┐
│ Freezing, thawing and obtaining the virus, and obtain the viral │
│ antigen                                                          │
└─────────────────────────────────────────────────────────────────┘
                                         ↓
┌─────────────────────────────────────────────┐
│           Determining virus titer           │
└─────────────────────────────────────────────┘
                                         ↓
┌──────────────────────────────────────────────────────────────────────────────────┐
│ Adding BEI until that the final concentration is 0.002M, inactivate for 24h at   │
│ 37 degree C, add sodium thiosulfate until that the final concentration is 0.5%   │
│ blocking the inactivation, and obtaining the semi-finished product for vaccine   │
└──────────────────────────────────────────────────────────────────────────────────┘
                                         ↓
┌──────────────────────────────────────────────────────────────────────────────────┐
│ Inspection of semi-finished product: sterility test and inactivation inspection  │
└──────────────────────────────────────────────────────────────────────────────────┘
                                         ↓
┌──────────────────────────────────────────────────────────────────────────────────┐
│ Vaccine preparation: taking inactivated antigen of PRV YF strain which passes    │
│ the inspection and adding the same into tween-80 with the final concentration    │
│ of 0.75%, and preparing the water phase after mixing and emulsifying according   │
│ to the proportion of the oil phase: water phase as 1.5:1. Adding the water phase │
│ into the oil phase slowly, homogenizing for 1-2 min, and then, preparing the     │
│ inactivated vaccine of porcine pseudorabies (PRV-YF strain)                      │
└──────────────────────────────────────────────────────────────────────────────────┘
                                         ↓
┌──────────────────────────────────────────────────────────────────────────────────┐
│ Inspection of semi-finished product: sterility test and nature inspection        │
└──────────────────────────────────────────────────────────────────────────────────┘
                                         ↓
┌─────────────────────────────────────────────────────┐
│ Safety evaluation and evaluation of immune efficacy │
└─────────────────────────────────────────────────────┘
```

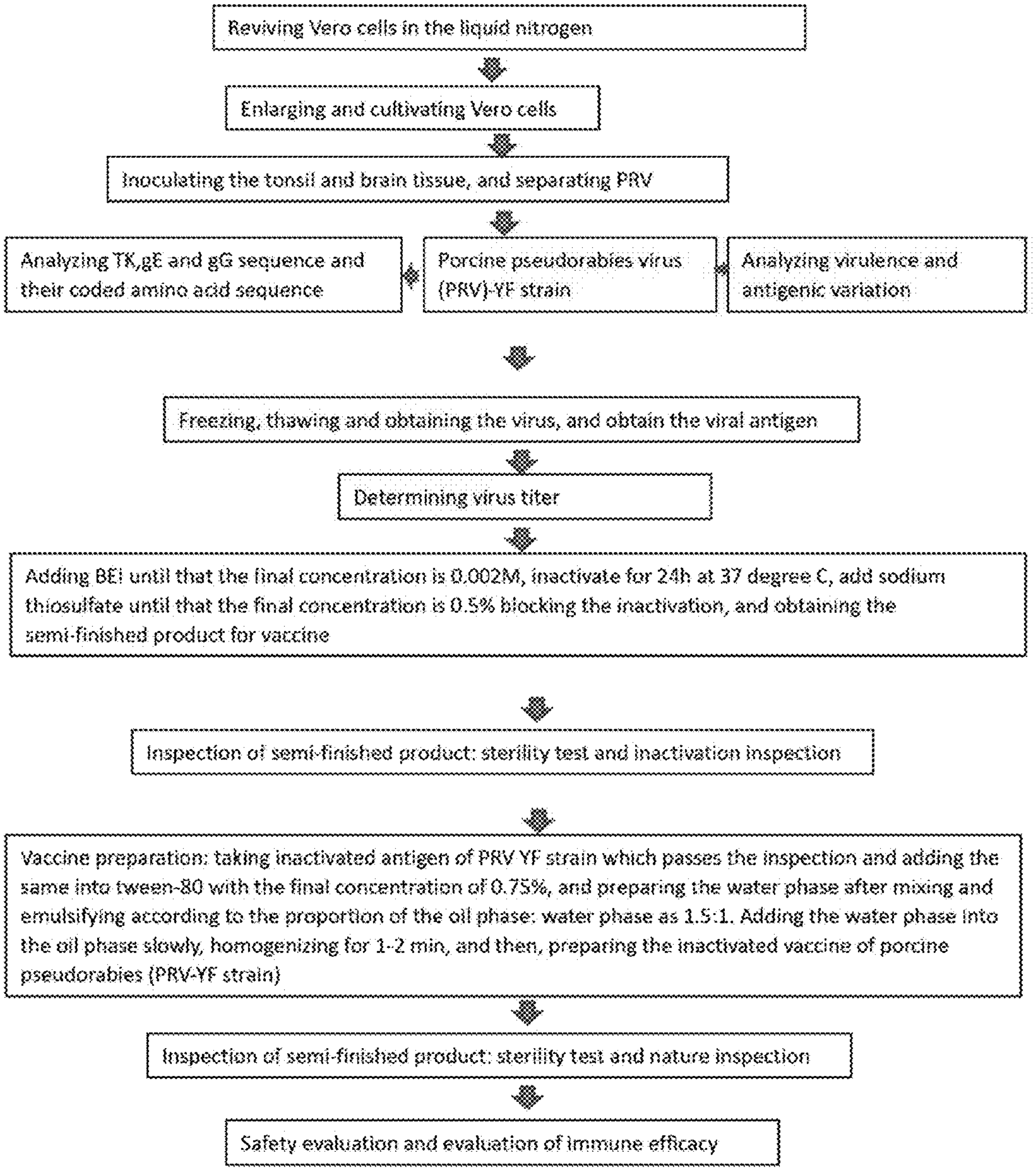

Figure 1

PORCINE PSEUDORABIES VIRUS (PRV)-YF STRAIN AND ITS APPLICATION

CROSS-REFERENCE TO RELATED APPLICATIONS

This application is a continuation of, and claims priority to, Chinese Patent Application No. 201510075712.4 with a filing date of Feb. 11, 2015. The content of the aforementioned application, including any intervening amendments thereto, is incorporated herein by reference.

SEQUENCE LISTING

This application contains, as a separate part of the disclosure, a Sequence Listing in computer-readable form (filename: D_ZQDX_00301_UUS_ST25.txt; created: Jan. 24, 2016: 4901 bytes—ASCII text file) which is incorporated by reference in its entirety.

TECHNICAL FIELD

The present invention relates to the technical field of porcine pseudorabies virus, and more particularly to a porcine pseudorabies virus (PRV)-YF strain, and also relates to the application of the porcine pseudorabies virus (PRV)-YF strain.

BACKGROUND

A pseudorabies virus (PRV) is a porcine herpesvirus type I in a Varicella virus of hepersviridae alpha-hepersririnae subfamily, capable of leading to serious porcine diseases. The PRV frequently outbreaks epidemically, seriously endangers pregnant swine in particular, and often results in fetal death, abortion and fetal mummies. Replacement gilts and non-pregnant sows infected with the PRV may be subjected to infertility, failure to observe oestrus, return to estrus and repeat breeder syndrome. Infected boars show such symptoms as testicular swelling, atrophy and loss of ability to inseminate. Mass mortality of newborn piglets infected with the PRV may be caused, in which the death rate of newborn piglets aged within 15 days may reach up to 100%, and the death rate of newborn piglets aged 3-4 weeks may reach up to 30-40%. Each of fattening swine infected with the PRV develops a fever, respiratory symptoms and growth retardation, resulting in affecting weight gain and reducing feed conversion. Meanwhile, pigs are natural host for the PRV and a source of infection to it. It may have a great significance to control the porcine pseudorabies on not only a pig industry, but also the smooth development of the culture of other animals. Vaccine immunization is a radical measure for the prevention, control and elimination of the PRV. A majority of PRV vaccines currently sold on the market are live vaccines having differential diagnosis capabilities, including a vaccine product of naturally attenuated strain Bartha-K61 developed in Hungaria, a PRV live vaccine (SA215 strain) developed by professor Guo Wanzhu at Sichuan Agricultural University, and a PRV live vaccine (HB98 strain) developed by professor Chen Huanchun at Huazhong Agricultural University. Those vaccines that have been put on the market for use for many years play an important role in prevention and control of the porcine pseudorabies. There are some reports on virus isolation occasionally, but the porcine pseudorabies has been effectively controlled in general.

However, since 2011, suspected PR has occurred epidemically on a number of large-scale pig farms in which gene deleted live vaccines are used for immunity. PR mainly shows such symptoms that swinery gE antibody positive rate is significantly increased, sows produce weak piglets and dead fetuses, and the piglets may be subjected to neural symptoms, death and the like. In particular, the piglets aged 2-3 days may be subjected to serious PR, with the time from onset to death for 5 hours only. Currently, the PR has spread to a number of provinces and regions in China, has killed a lot of piglets, and has made great economic losses.

Therefore, in the present invention, an epidemic (prevalent) strain is isolated clinically and is determined as porcine pseudorabies virus (PRV)-YF strain through a gene sequence analysis and an immune protection test; and BEI inactivation is performed after the propagation; an inactivated vaccine is prepared and the immune efficacy thereof is evaluated.

SUMMARY

In order to overcome the defects of the prior art, the aim I of the present invention is to provide a porcine pseudorabies virus (PRV)-YF strain.

The aim II of the present invention is to provide an application of the porcine pseudorabies virus (PRV)-YF strain in preparing an inactivated vaccine of the porcine pseudorabies virus.

The aim III of the present invention is to provide an inactivated PRV vaccine containing the porcine pseudorabies virus (PRV)-YF strain.

The aim IV of the present invention is to provide a preparation method for the inactivated vaccine of the porcine pseudorabies virus, so as to enhance the immune protective efficacy or safety of the inactivated vaccine through optimization of technological parameters.

In order to solve the above problems, the aims of the present invention are realized through the following technical solution:

In the present invention, the porcine pseudorabies virus (PRV)-YF strain is obtained through the separation from brains, tonsils and other tissues of pathogenetic piglets and the subculture adaptation; the porcine pseudorabies virus (PRV)-YF is submitted to the organization authorized by the patent for preservation, the preservation name is porcine pseudorabies virus (PRV)-YF strain, the preservation organization is China Center for Type Culture Collection (CCTCC), the preservation date is Jan. 21, 2015, the preservation No. is V201502, and the preservation address is Wuhan University of China.

Sequence analysis and antigenic variation analysis on TK, gE and gG genes are carried out on the isolated porcine pseudorabies virus (PRV)-YF strain, wherein 754 bp of TK gene segments and 578 bp of gE gene segments are respectively amplified in the tissue samples of tonsils and brains, which represents that the tonsils and the brains are PRV positive; after the PRV-YF strain is inoculated to Balb/C mice of 8-10 years old, the mice have the representations that the injected sites are pruritic, the hair is rough and disordered, and the spirit is depressed; nearly all the mice die, the symptoms such as pruritic injected sites, rough and disordered hair and depressed spirit are more obvious, the injected sites are scratched to be festered, the mice the one after another after 84 h, and the symptoms are more obvious. Therefore, the PRV-YF strain is determined to be a PRV clinical variant strain, and the existing live PRV vaccines do not completely protect immune animals against the PRV-YF strain.

The application of the porcine pseudorabies virus (PRV)-YF strain in preparing the inactivated vaccine of the porcine pseudorabies virus is described as follows:

The inactivated vaccine of the porcine pseudorabies virus comprises an adjuvant and virus liquid containing the inactivated porcine pseudorabies virus (PRV)-YF strain in claim 1.

The preparation method for the inactivated vaccine of the porcine pseudorabies virus comprises the following steps:

1) culturing the above-mentioned porcine pseudorabies virus (PRV)-YF strain of claim 1 to obtain a virus liquid;

2) adding an inactivator in the virus liquid for inactivating the virus; and then, adding a terminator for terminating inactivation to obtain an inactivated virus liquid of the PRV-YF strain; and 3) preparing a water phase and an oil phase and emulsifying to obtain the inactivated vaccine of the porcine pseudorabies virus.

Specifically, as an embodiment of the present invention, the virus content of the virus liquid prepared in Step 1) is not less than $10^{7.0}$ $TCID_{50}$/ml.

Specifically, as an embodiment of the present invention, the inactivator described in Step 2) is pyrrole; and weighing by w/v, the pyrrole added in the virus liquid accounts for 0.1% to 1% of the total amount of the virus liquid.

Specifically, as an embodiment of the present invention, the inactivation time is 12 to 60 h; and the inactivation temperature is 37° C.

Specifically, as an embodiment of the present invention, the terminator described in Step 2) is sodium thiosulfate; and weighing by w/v, the sodium thiosulfate added in the virus liquid accounts for 0.1% to 5% of the total amount of the virus liquid.

Specifically, as an embodiment of the present invention, weighing by w/v, the sodium thiosulfate added in the virus liquid accounts for 0.5% to 5% of the total amount of the virus liquid.

Specifically, as an embodiment of the present invention, Step 3) comprises the following steps:

A. Preparation of water phase: taking the inactivated virus liquid of the PRV-YF strain prepared in Step 2) and adding the same into Span-80 with the final concentration of 075%, mixing while adding until Span-80 is thoroughly dissolved, and preparing the water phase;

B. Preparation of oil phase: taking 141.75 parts of white oil, adding 7.5 parts of Span-80, fully mixing, sterilizing for 30 min at 121° C., cooling to room temperature for standby, and preparing the oil phase;

C. Emulsifying the oil phase and the water phase by 1.5:1; adding the water phase into the oil phase slowly, shearing after homogenizing for 1-3 min, and preparing a homogeneous emulsion, i.e., the inactivated vaccine of porcine pseudorabies.

Compared with the prior art, the present invention has the beneficial effects that:

The porcine pseudorabies virus (PRV)-YF strain isolated and identified in the brain, tonsil and other tissues of piglets has good immunogenicity. The live vaccine of existing porcine pseudorabies cannot be used for fully protecting the immune animal against the strain, but can be used as the porcine pseudorabies inactivated vaccine for producing and inspecting the strain; and the immune efficacy evaluation and safety evaluation are carried out on the water-in-oil inactivated vaccine prepared with the pathological liquid in PRV-YF strain, and the experiment shows that the porcine pseudorabies virus (PRV)-YF strain prepared in the invention has good immune efficacy, and is safe for weaned piglets, replacement gilts and pregnant sows. Therefore, it can be used for preventing the sow reproduction disorder and infertility arisen from porcine pseudorabies virus and pseudorabies of other pigs.

The present invention will be further described in detail below in combination with the drawings and specific embodiments.

DESCRIPTION OF DRAWINGS

FIG. 1 is a flow diagram of an embodiment of the present invention;

DETAILED DESCRIPTION OF EMBODIMENTS

Figure 2:
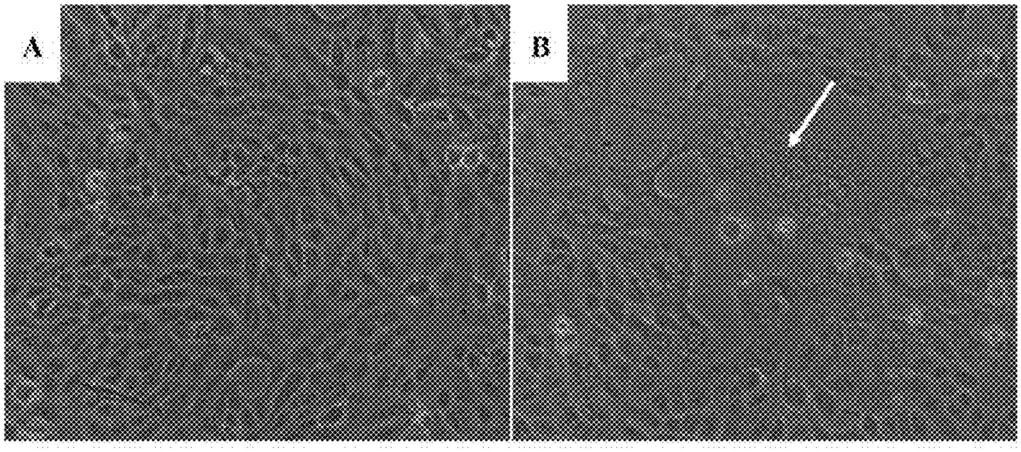
FIG. 2 is the observation of lesion of Vero cells, wherein A indicates the normal control cells, B indicates the pathological cells after virus inoculation, and the arrow indicates the pathological Vero cells.

Unless otherwise specified, all scientific and technical terminologies in the present application have the same meanings as those usually understood by those skilled in the art of the present invention. The following embodiments aim to further describe specific ways for realizing the present invention by examples, not interpreted as a limitation to the present invention. The technical solutions obtained by changing the present invention will fall into the scope of the claims of the present invention without departing from the spirit and the principle of the present invention.

Embodiment 1 Isolation and Identification of Variant Train of Porcine Pseudorabies Virus 1. Material 1.1 Cell, Virus and Vaccine The Ra strain (*Study on proliferativen characteristics and pathogenicity of Ra strain of pseudorabies virus to different cells*, Yu Wenlan, etc., China Animal Husbandry & Veterinary Medicine, Vol. 11, 2013) of typical virulent strain of Vero cell, PK15 cell and porcine pseudorabies virus are stored in the key laboratory created by the animal epidemic disease control biotechnology and product of Ministry of Agriculture of Zhaoqing Dahuanong Biotechnology Co., Ltd.; and the live vaccine (K-61 strain) of porcine pseudorabies is an product from Guangdong Dahuanong Animal Health Products Co., Ltd.

1.2 Pathological Material

Tonsil and brain tissue of piglets in a pig farm in Xinxing County, Yunfu City.

1.3 Medium and Other Reagents

The fetal calf serum and DMEM medium are purchased from Gibco Company, the virus DNA/RNA extraction reagent kit is purchased from Biomiga Company, and LA Taq enzyme reagent kit is purchased from TaKaRa Company.

1.4 Experimental Animal

Balb/C mice with 8-10 weeks of age are purchased Guangdong Medical Laboratory Animal Center.

1.5 Primer

The premier is designed and synthesized by referring to a whole genome sequence (NC_006151) of porcine pseudorabies virus, and used for amplifying PRV gE and gG whole genes. The primer sequence and the size of expected PCR product are shown in Table 1, TKF/TKR and gEF/gER are PRV TK and gE gene detection primer (refer to the applied patent: 201210128876.5).

TABLE 1

PCR primers for detecting PRV and amplifying PRV gE and gG whole genes

| Primer | 5'-3' | Size/ bp | Target segment |
|---|---|---|---|
| TKF<br>TKR | ATGCGCATCCTCCGGATCTACCT<br>TTCCGCCTCAGAAGCCATAGAGC | 754 | TK gene detection |
| gEF<br>gER | ATGCGGCCCTTTCTGCTGCG<br>TGCAGCGTGTAGAGGCCCGT | 578 | gE gene detection |
| gE-CDSF<br>gE-CDSR | ATGCGGCCCTTTCTGCTGCG<br>TTAAGCGGGGCGGGCATTCAA | 1742 | gE whole gene detection |
| gG-CDSF<br>gG-CDSR | CTCAACAATGAAGTGGGCAACG<br>TCAGGCGGAGGCCACGT | 1507 | gG whole gene amplification |

2. Disposal of Pathological Material and PRV Detection

The tonsil and brain tissue of the pathogenetic piglets are added into a suspension prepared by grinding and blending sterile PBS by 1:3, repeatedly frozen and thawed for three times, and centrifuged for 15 min at 5000 r/min; and the supernate is taken, wherein a part is filtered through 0.45 μL and 0.22 μL microporous membrane respectively and stored at −70° C. for standby, and virus DNA is extracted from the other part according to a virus DNA extraction reagent kit; then, PRV TK and gE genes are detected with primers TKF/TKR and gEF/gER in Table 1 respectively; the pathological material which is detected for being positive is used for the virus isolation, and PCR reaction system and reaction condition are as follows:

PCR reaction system and reaction condition of TK and gE gene detection

| | | | |
|---|---|---|---|
| Genome DNA | 1 ul | 94° C. 3 min | 1 cycle |
| 2 × GC Buffer I (5 mM Mg2+ plus) | 12.5 ul | 98° C. 10 sec | 30 cycles |
| Upstream primer | 0.5 ul | 60° C. 30 sec | |
| Downstream primer | 0.5 ul | 72° C. 30 sec | |
| dNTP Mixture (2.5 mM each) | 4 ul | 72° C. 7 min | 1 cycle |
| TaKaRa LA Taq (5 U/ul) | 0.5 ul | | |
| dH2O | 6 ul | | |

The results show that, 754 bp TK gene segment and 578 bp gE gene segment are amplified by tonsil and brain tissue samples respectively, which indicates that the tonsil and the brain tissue are PRV positive.

3. Virus Isolation

The Vero cells are cultured according to a conventional method; and the single-layer dense Vero cells are digested the day before inoculating, inoculated into a 6-hole cell culture plate, with 2 ml for each hole, and cultured in 5% $CO_2$ at 37° C. until to the next day, wherein more than 80% cells are intersected. 200 μL sterile viral suspensions of tissues are taken and inoculated into a Vero monolayer cell in the 6-hole plate, and replaced with a DMEM culture solution including 2% fetal calf serum after incubating for 1 h, and the cytopathic effect (CPE) is observed day by day. See FIG. 2. The toxin is received by freezing and thawing when about 90% cells have the CPE.

4. Virus Purification

The plaque of a recombinant virus is purified according to the conventional method; the monolayer cell which is grown well is digested and inoculated into the 6-hole culture plate, and cultured in 5% $CO_2$ at 37° C. until to grow into a single layer; the virus liquid is diluted to $10^{-7}$ by 10 times; the latter four diluted viruses are taken, inoculated into the monolayer cell in the 6-hole plate, with one hole for each dilutability, and cultured in 5% $CO_2$ at 37° C. for 1 h to 2 h; the virus liquid is sucked and abandoned, and washed for 3 times with DMEM; and 1.5 ml phenol red-free including 2% to 5% serum and 2% low-melting-point agar is covered and cultured in 5% $CO_2$ at 37° C. till to observe the obvious lesion. The second layer of agar, i.e. phenol red-free DMEM including 2% low-melting-point agar and 0.01% neutral red, is covered and incubated in 5% $CO_2$ at 37° C., the obvious plaque is seen with naked eyes, and the plaque is picked as required. A variant strain of porcine pseudorabies virus is obtained by purifying for 2 times, and named as the PRV-YF strain.

5. Propagation of PRV-YF Strain and Ra Strain and Determination of $TCID_{50}$

The PRV-YF strain and the Ra strain are propagated according to the conventional method, namely, the viral suspension of the PRV-YF strain and the Ra strain is inoculated into a T175 culture flask to overgrow the monolayer Vero cells; and the virus liquid is received by freezing and thawing when culturing in 5% $CO_2$ at 37° C. till that the lesion is more than 90%. The received virus liquid is diluted to $10^{-8}$ by 10 times, 8 holes are repeated for each dilutability, the virus liquid is inoculated into a 96-hole plate with the Vero cells synchronously and cultured in 5% $CO_2$ at 37° C. until that the number of pathological holes is not changed; the number of pathological holes in each dilutability is read, and $TCID_{50}$ is calculated according to Reed-Muench method. The result is shown in Table 2, $TCID_{50}$ of the PRV-YF strain is $10^{7.43}$/mL, and $TCID_{50}$ of the Ra strain is $10^{7.33}$/mL.

TABLE 2

Determination of $TCID_{50}$ of PRV-YF strain and Ra strain

| | PRV-YF strain ($TCID_{50} = 10^{6.43}$/0.1 mL) | | | | | PRV Ra strain ($TCID_{50} = 10^{6.33}$/0.1 mL) | | | | |
|---|---|---|---|---|---|---|---|---|---|---|
| Dilutability | Number of lesion | Normal number | Total number of lesion | Total normal number | Lesion rate (%) | Number of lesion | Normal number | Total number of lesion | Total normal number | Lesion rate (%) |
| $10^{-1}$ | 8 | 0 | 47 | 0 | 100 | 8 | 0 | 46 | 0 | 100 |
| $10^{-2}$ | 8 | 0 | 39 | 0 | 100 | 8 | 0 | 38 | 0 | 100 |

TABLE 2-continued

| Determination of $TCID_{50}$ of PRV-YF strain and Ra strain | | | | | | | | | | |
|---|---|---|---|---|---|---|---|---|---|---|
| | PRV-YF strain ($TCID_{50} = 10^{6.43}$/0.1 mL) | | | | | PRV Ra strain ($TCID_{50} = 10^{6.33}$/0.1 mL) | | | | |
| Dilutability | Number of lesion | Normal number | Total number of lesion | Total normal number | Lesion rate (%) | Number of lesion | Normal number | Total number of lesion | Total normal number | Lesion rate (%) |
| $10^{-3}$ | 8 | 0 | 31 | 0 | 100 | 8 | 0 | 30 | 0 | 100 |
| $10^{-4}$ | 8 | 0 | 23 | 0 | 100 | 8 | 0 | 22 | 0 | 100 |
| $10^{-5}$ | 8 | 0 | 15 | 0 | 100 | 8 | 0 | 14 | 0 | 100 |
| $10^{-6}$ | 7 | 1 | 7 | 1 | 87.5 | 6 | 2 | 6 | 2 | 75 |
| $10^{-7}$ | 0 | 8 | 0 | 9 | 0 | 0 | 8 | 0 | 10 | 0 |
| $10^{-8}$ | 0 | 8 | 0 | 17 | 6 | 0 | 8 | 0 | 18 | 0 |

6. Determination of Virulence and Antigenic Variation of Mice 6.1 Determination of Virulence of Mice 78 Balb/C mice with 8-10 weeks of age are randomly divided into 13 groups, 6 mice in each group; the viral suspensions of the PRV-YF strain and the Ra strain are diluted to $10^{6.0}$, $10^{5.0}$, $10^{4.0}$, $10^{3.0}$, $10^{2.0}$ and $10^{1.0}$ $TCID_{50}$/0.5 mL respectively, wherein each dose is provided for one group of Balb/C mice, totally 12 groups, and the other group is the blank control group. The situation of the mice and the number of deaths are observed every day after inoculating, and $LD_{50}$ is calculated according to the Reed-Muench method.

TABLE 3

| Virulence test of Porcine pseudorabies virus (PRV) -YF strain and Ra strain to mice | | | | | | | | | | |
|---|---|---|---|---|---|---|---|---|---|---|
| | ($TCID_{50}$) Challenge viral dosage | Number of accumulative deaths | | | | | | | | |
| Virus | ($TCID_{50}$) | 24 h | 36 h | 48 h | 60 h | 72 h | 84 h | 96 h | 108 h | 120 h |
| PRV-YF strain | $10^{6.0}$ | 0/6 | 0/6 | 5/6 | 6/6 | | | | | |
| $LD_{50} = 10^{2.25}$TCI | $10^{5.0}$ | 0/6 | 0/6 | 0/6 | 5/6 | 6/6 | | | | |
| $D_{50}$ | $10^{4.0}$ | 0/6 | 0/6 | 0/6 | 5/6 | 6/6 | | | | |
| | $10^{3.0}$ | 0/6 | 0/6 | 0/6 | 1/6 | 4/6 | 6/6 | | | |
| | $10^{2.0}$ | 0/6 | 0/6 | 0/6 | 0/6 | 0/6 | 0/6 | 1/6 | 2/6 | |
| | $10^{1.0}$ | 0/6 | 0/6 | 0/6 | 0/6 | 0/6 | 0/6 | 0/6 | 0/6 | 0/6 |
| PRV Ra strain | $10^{6.0}$ | 0/6 | 0/6 | 0/6 | 6/6 | | | | | |
| $LD_{50} = 10^{2.12}$TCI | $10^{5.0}$ | 0/6 | 0/6 | 0/6 | 2/6 | 4/6 | 6/6 | | | |
| $D_{50}$ | $10^{4.0}$ | 0/6 | 0/6 | 0/6 | 0/6 | 5/6 | 6/6 | | | |
| | $10^{3.0}$ | 0/6 | 0/6 | 0/6 | 0/6 | 0/6 | 3/6 | 5/6 | | |
| | $10^{2.0}$ | 0/6 | 0/6 | 0/6 | 0/6 | 0/6 | 3/6 | | | |
| | $10^{1.0}$ | 0/6 | 0/6 | 0/6 | 0/6 | 0/6 | 0/6 | 0/6 | 0/6 | 0/6 |
| Control group | | 0/6 | 0/6 | 0/6 | 0/6 | 0/6 | 0/6 | 0/6 | 0/6 | 0/6 |

Note: 0/6 indicates that 6 mice do not die; 2/6 indicates that 2 in 6 mice die, and others are analogized.

Figure 3:
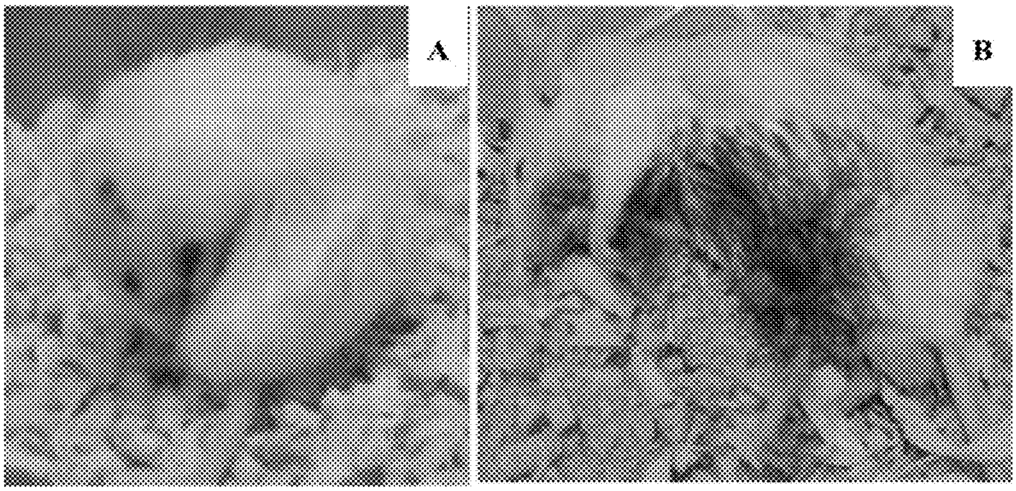
FIG. 3 indicates that the mice mainly show the pruritus after challenge, wherein A indicates the injection site that the mice scratch and bite, and B indicates that the injection site is bitten until to be ruptured.

No any abnormality is presented in the control group by continuously observing for 120 h after inoculating. All toxic mice are normal in 36 h after inoculating; 5 mice die in $10^{6.0}$ $TCID_{50}$ group of the PRV-YF strain in 36 h to 48 h, the mice in $10^{5.0}$, $10^{4.0}$ and $10^{3.0}$ $TCID_{50}$ groups show the pruritus of injection site, coarse and messy hair and depressed spirit; no death is presented in the toxic group of the Ra strain, but the high dose group also shows the pruritus of injection site, coarse and messy hair, depressed spirit and other symptoms; the mice has the most intense reaction in 48 h to 72 h; the mice in $10^{3.0}$ $TCID_{50}$ group and above almost die completely, the pruritus of injection site, coarse and messy hair, depressed spirit and other symptoms are more obvious, and the injection site is scratched to fester, as shown in FIG. 3; and the mice die continuously after 84 h, and the symptom is obvious. The death of the mice is shown in Table 3 according to the time accumulation, LD50 of the PRV-YF strain is $10^{2.25}$ $TCID_{50}$, and $LD_{50}$ of the Ra strain is $10^{2.12}$ $TCID_{50}$; and no obvious difference is presented by $LD_{50}$ of the two strains, but in combination with the time of symptom expression of mice and death time, it can be seen that the virulence of the PRV-YF strain is slightly enhanced compared with that of the Ra strain.

6.2 Analysis of Antigenic Variation

30 Balb/C mice with 8-10 weeks of age are randomly divided into 5 groups, 6 mice for each group. Two groups are live vaccine (K-61 strain) of immune porcine pseudorabies, other groups are not immunized, and the secondary immunization is carried out after 3 weeks of primary immunization. The blood sampling is carried out in 2 weeks after the secondary immunization, a neutralizing antibody of PRV is detected with PK15 cells according to the conventional method, the neutralizing antibody of the immunized mice is not less than 1:20, the neutralizing antibody of the mice in the control group is less than 1:4, and the result is shown in Table 4. After the blood sampling, the immunized mice in the two groups are virulently attacked with the PRV-YF strain and the Ra strain respectively, the dose is 100 $LD_{50}$/PCS, and at the same time, the toxic control group is provided, and a blank control group is provided. The result is shown in Table 4, and after challenge for 120 h, the mice in the non-immunized and non-attack control group are normal, and the mice in the toxic control group die completely; after the mice immunized by the vaccine attacks the PRV Ra strain, the individual mice have slight pruritus only, and others are healthy and living completely; and after the mice immunized by the vaccine attacks the PRV-YF strain, 3 mice die, and others have slight pruritus.

TABLE 4

Detection of neutralizing antibody after immunization of live vaccine (K-61 strain) of porcine pseudorabies and number of death of mice after challenge

| Challenge virulence | Vaccine immunity | Detection of neutralizing antibody in 2 weeks after the secondary immunization | Number of accumulative deaths after challenge for 120 h |
|---|---|---|---|
| PRV-YF strain | K-61 strain | 1:25, 1:22, 1:25, 1:30, 1:26, 1:32 | 3 mice die, and others show the slight pruritus. |
| | Non-immunized | The neutralizing antibody of 6 mice is less than 1:4 | 6 mice die completely |
| PRV Ra strain | K-61 strain | 1:20, 1:24, 1:26, 1:22, 1:33, 1:24 | 6 mice are healthy and living; and the individual mice only have slight pruritus. |
| | Non-immunized | The neutralizing antibody of 6 mice is less than 1:4 | 6 mice die completely |
| Non-immunized and non-attack control group | | The neutralizing antibody of 6 mice is less than 1:4 | 6 mice are normal |

7. Amplification and Analysis of gE and gG Whole-Genome Sequence

A PRV genome is extracted from the purified virus suspension of the PRV-YF strain with the virus gene extraction reagent kit; then, PRV gE and gG whole genes are amplified with the primers gECDSF/gECDSR and gGCDSF/gGCDSR in Table 1 respectively; the pathological material which is detected for being positive is used for the virus isolation, and PCR reaction system and reaction condition are as follows:

| PCR reaction system and reaction condition of gE and gG whole gene amplification | | | |
|---|---|---|---|
| Genome DNA | 1 ul | 94° C. 3 min | 1 cycle |
| 2 x GC Buffer I (5 mM Mg2+ plus) | 12.5 ul | 98° C. 10 sec | 30 cycles |
| Upstream primer | 0.5 ul | 50° C. 30 sec | |
| Downstream primer | 0.5 ul | 72° C. 2 min | |
| dNTP Mixture (2.5 mM each) | 4 ul | 72° C. 7 min | 1 cycle |
| TaKaRa LA Taq (5 U/ul) | 0.5 ul | | |
| $dH_2O$ | 6 ul | | |

Figure 4:
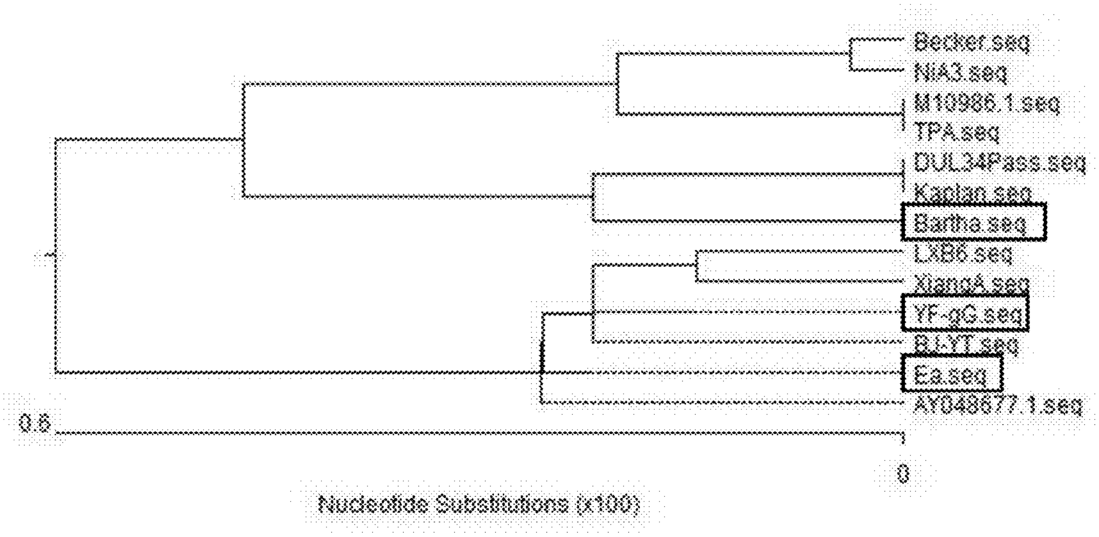
FIG. 4 is an analysis diagram for evolution of gE whole gene of PRV-YF strain described in the present invention.
Figure 5:
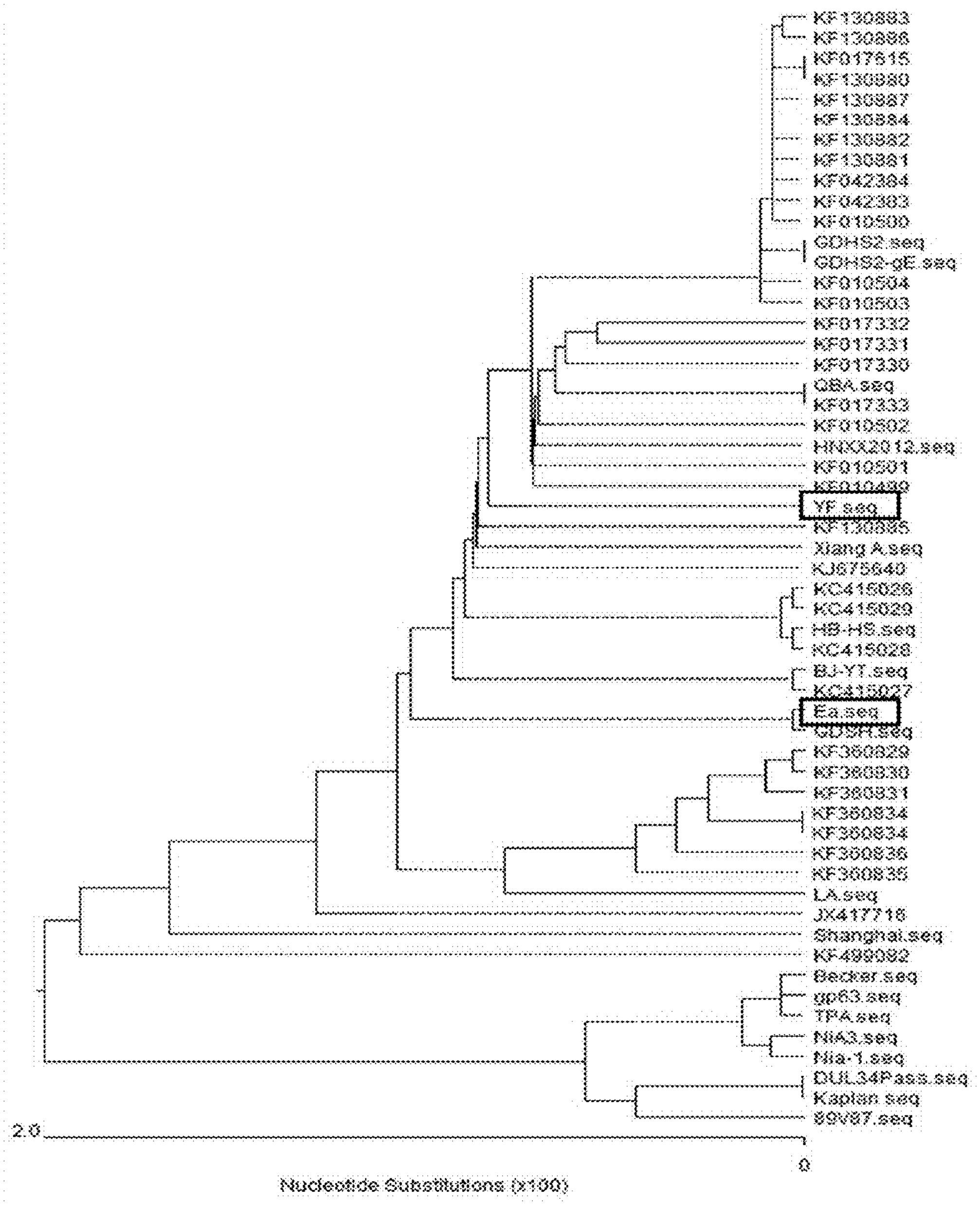
FIG. 5 is an analysis diagram evolution of gG whole gene of PRV-YF strain described in the present invention.

DNA star MegAlign software is adopted for the molecular evolution analysis of gE and gG whole genes.

gE whole-genome sequence is shown in SEQ ID No. 1, and the evolution analysis is shown in FIG. 4; and gG whole-genome sequence is shown in SEQ ID No. 2, and the evolution analysis is shown in FIG. 5.

The results of the molecular evolution analysis show that gE gene and gG gene of the PRV-YF strain have high homology with domestic strain, but are located in independent subbranches, and not located in the same branch with a Bartha K-61 strain of vaccine strain and an Ea strain of female parent strain of an HB98 strain, which indicates that the PRV-YF strain isolated clinically is indeed different from a typical strain.

8. Conclusion

A porcine pseudorabies virus is isolated from the tonsil and the brain tissue of the clinical pathological material according to the present invention, and named as the porcine pseudorabies virus (PRV)-YF strain; and through the sequence analysis of gE and gG genes and analysis for antigenic variation of virus, the PRV-YF strain is determined as the clinical variant strain of porcine pseudorabies virus, and the live vaccine of existing porcine pseudorabies cannot be used for fully protecting the immune animal against the strain.

Embodiment 2 Preparation of Inactivated Vaccine of Porcinepseudorabies (PRV-YF Strain)

1. Material 1.1 Virus and Cell

The porcine pseudorabies virus (PRV)-YF strain is prepared in Embodiment 1 and the Vero cells are stored in the key laboratory created by the animal epidemic disease control biotechnology and product of Ministry of Agriculture of Zhaoqing Dahuanong Biotechnology Co., Ltd.

1.2 Medium and Other Reagents

The fetal calf serum and DMEM medium are purchased from Gibco Company; the white oil is purchased from Mobil Corporation, and the Tween-80 and Span-80 are purchased from Guangdong Zhaoqing Chaoneng Industrial Co., Ltd.; 2-bromoethyl amine hydrobromide is purchased from TCI (shanghai) Development Co., Ltd.; and sodium thiosulfate is domestic and analytically pure.

2. Proliferation of Porcine Pseudorabies Virus (PRV)-YF Strain

The viral suspension of the PRV-YF strain is inoculated into 80% fused Vero cells according to the conventional method of pseudorabies virus multiplication, its $TCID_{50}$ is determined according to the conventional method when culturing until that lesion reaches 100%, and the result is shown in Table 5. $TCID_{50}$ of the PRV-YF strain is $10^{7.57}$/mL, which indicates that the multiplication of the PRIG-YF strain is good.

TABLE 5

Determination of $TCID_{50}$ of PRV-YF strain

| Dilutability | PRV-YF strain ($TCID_{50}$ = $10^{6.57}$/0.1 ml) Number of lesion | Normal number | Total number of lesion | Total normal number | Lesion rate (%) |
|---|---|---|---|---|---|
| $10^{-1}$ | 8 | 0 | 49 | 0 | 100 |
| $10^{-2}$ | 8 | 0 | 41 | 0 | 100 |
| $10^{-3}$ | 8 | 0 | 33 | 0 | 100 |
| $10^{-4}$ | 8 | 0 | 25 | 0 | 100 |
| $10^{-5}$ | 8 | 0 | 17 | 0 | 100 |

TABLE 5-continued

| Determination of $TCID_{50}$ of PRV-YF strain | | | | | |
|---|---|---|---|---|---|
| | PRV-YF strain ($TCID_{50} = 10^{6.57}$/0.1 ml) | | | | |
| Dilutability | Number of lesion | Normal number | Total number of lesion | Total normal number | Lesion rate (%) |
| $10^{-6}$ | 8 | 0 | 9 | 0 | 100 |
| $10^{-7}$ | 1 | 7 | 1 | 7 | 12.5 |
| $10^{-8}$ | 0 | 8 | 0 | 15 | 0 |

3. Determination of Inactivation Condition of Porcine Pseudorabies Virus (PRV)-YF Strain 3.1 Preparation of Inactivator:

2-bromoethyl amine hydrobromide (BEA) powder is added into 0.2 mol/L sodium hydroxide solution prepared newly, placed in water bath at 37° C., and shaken out once every 10 min; cyclizing is stopped when a pH value is reduced to 8.0 after 30 min to 60 min; and pyrrole (BEI) with the final concentration of 0.2 mol/L is prepared, and placed at 2 to 8° C. for storage and standby after aseptic filtration.

3.2 Determination of Inactivation Condition of BEI

The test is carried out in accordance with the following solution. See Table 6:

TABLE 6

| Probe test solution of inactivation condition of inactivator BEI | | |
|---|---|---|
| Inactivation temperature (° C.) | Concentration of inactivator (M) | Inactivation time (h) |
| 37 | 0.001 | 12, 20, 24, 30, 36, 48 |
| | 0.002 | |
| | 0.005 | |
| 32 | 0.001 | 12, 20, 24, 30, 36, 48 |
| | 0.002 | |
| | 0.005 | |

After testing the virus liquid of the PRV-YF strain according to the above solution, the inactivated sample is inoculated into the Vero cells, the situation of cytopathic effect is observed, the non-pathological cells are subjected to the blind passage for 3 generations and observed continuously, and the results are shown in Table 7. In order to ensure the vaccine quality and guarantee that the viral antigen in the vaccine is fully inactivated, the inactivation condition of the PRV-YF strain is determined to inactivate in BEI with the final concentration of 0.002M at 37° C. for 24 h.

TABLE 7

| Test result of inactivation condition of inactivator BEI | | | | | | |
|---|---|---|---|---|---|---|
| Inactivation | 37° C. | | | 32° C. | | |
| time (h) | 0.001 M | 0.002 M | 0.005 M | 0.001 M | 0.002 M | 0.005 M |
| 12 | + | − | − | + | + | − |
| 20 | + | − | − | + | + | − |
| 24 | − | − | − | + | − | − |
| 30 | − | − | − | + | − | − |
| 36 | − | − | − | + | − | − |
| 48 | − | − | − | + | − | − |

Note: + indicates the cytopathic effect, and − indicates no cytopathic effect.

3.3 Determination of Terminator Sodium Thiosulfate ($Na_2S_2O_3$)

The virus liquid of the PRV-YE strain is inactivated with 0.002M BEI for 24 h at 37° C., and the activity of BEI is stopped with the $Na_2S_2O$ with the final concentration (W/V) for 0.01% to 5%. BEI inactivates the virus mainly by acting on the viral nucleic acid, and the residual BEI is able to act on the cells while the inactivation inspection, thus, causing the cell death or poor growth, therefore, the activity of BEI is stopped before the inactivation inspection. The results show that, the activity of BEI cannot be fully neutralized when the final concentration of $Na_2S_2O_3$ is less than 0.5%, and after the inactivation is stopped and the Vero cells are inoculated into an antigen solution, the cells are grown slowly, and the continuous passage is impossible; and when the final concentration of $Na_2S_2O_3$ is not less than 0.5%, the activity of BEI can be fully neutralized, and after the inactivation is stopped and the Vero cells are inoculated into the antigen solution, the cells are grown normally, and the continuous passage is normal. Therefore, the final concentration of terminator $Na_2S_2O_3$ is determined to be not less than 0.5%.

4. Inspection of Semi-Finished Product 4.1 Inspection of Virus Content $TCID_{50}$ of the PRV-YF strain is determined according to the conventional method after the viral multiplication, and the content of 1 ml virus is not less than $10^{7.0}$ $TCID_{50}$.

4.2 Inactivation Inspection

The inactivated virus liquid is inoculated into the Vero cells by 10% synchronously for continuous passage for 3 times, without the cytopathic effect.

4.3 Sterility Test

The sterility test is carried out in accordance with the current appendix of *Chinese Veterinaty Pharmacopoeia* and no bacterial growth is provided.

5. Preparation of Inactivated Vaccine of Porcine Pseudorabies PRS-YF Strain)

5.1 Preparation of Water Phase

The inactivated antigen of the PRV-YF strain which passes the inspection is taken and added into Tween-80 with the final concentration of 0.75% (taking the milliliter as the unit), and mixed while adding until Tween-80 is thoroughly dissolved; and the water phase is prepared.

5.2 Preparation of Oil Phase 141.75 parts of white oil (taking the milliliter as the unit) are taken, added into 7.5 parts of Span-80 (taking the milliliter as the unit), fully mixed, sterilized for 30 min at 121° C., and cooled to room temperature for standby.

5.3 Emulsification by the Proportion of the Oil Phase to the Water Phase as 1.5:1

The water phase is added into the oil phase slowly, sheared after homogenizing for 1-3 min; and a homogeneous emulsion is prepared, i.e. inactivated gene vaccine of porcine pseudorabies.

6. Finished Product Inspection of Vaccine 6.1 Nature Inspection

The water-in-oil milk white emulsion is dripped on the surface of cold water and not dispersed, the vaccine is centrifuged for 15 min at 3000 r/min, no water phase is separated out at the bottom of a pipe, and the viscosity is 27.5 cP.

6.2 Sterility Test

The sterility test is carried out in accordance with the current appendix of *Chinese Veterinary Pharmacopoeia*, and no bacterial growth is provided.

Embodiment 3 Detection for Immune Efficacy and Safety of Inactivated Vaccine of Porcine Pseudorabies (PRV-YF Strain)

I. Evaluation of Immune Efficacy of Inactivated Vaccine of Porcine Pseudorabies (PRV-YF Strain) with Mice As pesudorabies virus can cause the obvious clinical symptom and death of the mice, it is convenient for clearly judging the immune efficacy of inactivated vaccine of porcine pseudorabies (PRV-YF strain).

1. Material 1.1 Virus and Cell

The YF strain and Vero cells of porcine pseudorabies virus are stored in the key laboratory created by the animal epidemic disease control biotechnology and product of Ministry of Agriculture of Zhaoqing Dahuanong Biotechnology Co., Ltd.

1.2 Experimental Animal

Balb/C female mice with 4-6 weeks of age are purchased from Guangdong Medical Laboratory Animal Center, and used for evaluating the immune efficacy of inactivated vaccine of porcine pseudorabies (PRV-YF strain).

1.3 Reagent

The fetal calf serum and DMEM medium are purchased from Gibco Company.

2. Determination of Immune Efficacy of Inactivated Vaccine of Porcine Pseudorabies (PRV-YF Strain)

2.1 Test Solution

Totally, 36 Balb/C female mice with 4-6 weeks of age are divided into 6 groups, 6 mice in each group. The specific solution is shown in Table 8:

TABLE 8

Test solution of immune efficacy

| Immunizing dose (ml/PCS) | Times of immunization | Number of animals |
|---|---|---|
| 0.5 | Primary immunization | 6 |
| | Secondary immunization | 6 |
| 1.0 | Primary immunization | 6 |
| | Secondary immunization | 6 |
| Non-immune toxic control group | | 6 |
| Blank control group | | 6 |

The secondary immunization is carried out in 4 weeks after the primary immunization. In 2 weeks after the secondary immunization, 100 $LD_{50}$ (about $10^{4.25}$ $TCID_{50}$) PRV-YF strain is used for attacking, and the continuous observation is carried out for 14 days after the challenge.

2.2 Test Result

As shown in Table 9, all immunized mice are normal after the immunization; after the challenge for 48 h, the mice in the non-immune toxic control group show the pruritus, neurological symptom, anorexia and coarse and messy hair; the death is presented after 60 h, until that 6 mice in the whole group die completely in 96 h; and in the whole observation period after the challenge, all immunized mice are normal, which indicates that the inactivated vaccine of porcine pseudorabies (PRV-YF strain) in the present invention has good immune protective efficacy.

TABLE 9

Experimental result of immune efficacy

| Immunizing dose (ml/PCS) | Times of immunization | Number of animals | Number of accumulative deaths 48 h | 72 h | 96 h | 120 h | 144 h |
|---|---|---|---|---|---|---|---|
| 0.5 | Primary immunization | 6 | –/6 | –/6 | –/6 | –/6 | –/6 |
| | Secondary immunization | 6 | –/6 | –/6 | –/6 | –/6 | –/6 |
| 1.0 | Primary immunization | 6 | –/6 | –/6 | –/6 | –/6 | –/6 |
| | Secondary immunization | 6 | –/6 | –/6 | –/6 | –/6 | –/6 |
| Non-immune toxic control group | | 6 | –/6 | 5/6 | 6/6 | | |
| Blacnk control group | | 6 | –/6 | –/6 | –/6 | –/6 | –/6 |

Note: –/6 indicates no death; 1/6 indicates that one mouse dies in 6 mice, and others are analogized.

II. Safety Evaluation of Inactivated Vaccine of Porcine Pseudorabies (PRV-YF Strain)

1. Experimental Animal 30 weaned piglets with negative porcine pseudorabies virus antibody, 30 replacement gilts and 30 pregnant sows are respectively purchased from the pig breeding farm of Wens Group.

2. Test solution: the reaction situation of the pig is carefully observed after immunizing neck muscles according to the above solution, and continuous observation is carried out for 21 days.

TABLE 10

Test solution of safety evaluation

| Animal | Inoculation method | Inoculation dose | Number of animals |
|---|---|---|---|
| Weaned piglets | Primary inoculation with single dose | 2 ml/pig | 5 pigs |
| | Repeated inoculation with single dose | 2 ml/pig, interval of 3 weeks | 5 pigs |
| | Primary inoculation with super times of dose | 4 ml/pig | 5 pigs |
| | Control | | 5 pigs |
| Replacement gilts | Primary inoculation with single dose | 2 ml/pig | 5 pigs |
| | Repeated inoculation with single dose | 2 ml/pig, interval of 2 weeks | 5 pigs |
| | Primary inoculation with super times of dose | 4 ml/pig | 5 pigs |
| | Control | | 5 pigs |
| Pregnant sows | Primary inoculation with single dose | 2 ml/pig | 5 pigs |
| | Repeated inoculation with single dose | 2 ml/pig, interval of 2 weeks | 5 pigs |
| | Primary inoculation with super times of dose | 4 ml/pig | 5 pigs |
| | Control | | 5 pigs |

2. Safety Evaluation Test Result

As shown in Table 11, the results show that, the weaned piglets with 25 days old are subjected to the primary inoculation of vaccine with single dose, primary inoculation with super times of dose and repeated inoculation with single dose. The inoculation site of immunized piglets is not swollen, no abnormality is provided in the whole body, and all piglets are healthy and living. All experimental pigs are grown normally in the process of feeding, and have no accidental death and disease. Meanwhile, the young replacement gilts with 6 months of age are subjected to the primary inoculation of vaccine with single dose, primary inoculation with super times of dose and repeated inoculation with single dose. The inoculation site of immunized pigs is not swollen, no abnormality is provided in the whole body, and all pigs are healthy and living. All experimental pigs are grown normally in the process of feeding, and have no accidental death and disease. The results show that, the vaccine provided by the present invention is safe for the young replacement gilts with 6 months of age, regardless of primary inoculation with single dose, primary inoculation with super times of dose and repeated inoculation with single dose.

The results in Table 12 show that, one sow is aborted after inoculating for 15 days in the experimental group that the pregnant sows are subjected to the primary inoculation with single dose; and the control group that the primary inoculation with super times of dose, repeated inoculation with single dose and repeated injection of normal saline with single dose are carried out has no abnormal reaction. The aborted fetus is detected, PRV is not separated, and after analysis, the reason of abortion shall be attributed to the mechanical stimulation in the process of injecting the vaccine and grasping the pigs or other reasons, rather than the vaccine itself. Thus, it can be seen that, the vaccine is safe for the pregnant sows. All experimental pigs are grown normally in the process of feeding, and have no accidental death and disease. The results show that, the vaccine provided by the present invention is safe for the pregnant sows.

TABLE 11

Results of safety test of weaned piglets and replacement gilts

| Animal | Immunization way | Quantity | Age in days | Inoculation route | Injection dose | Times of immunization | Observation items: General reaction | Observation items: Injection site | Result |
|---|---|---|---|---|---|---|---|---|---|
| Weaned piglets | Primary inoculation with single dose | 5 pigs | 25 | Neck muscle injection | 2 ml/pig | 1 | No abnormality | No swelling | 5/5 is health and living |
| | Primary inoculation with super times of dose | 5 pigs | 25 | Neck muscle injection | 4 ml/pig | 1 | No abnormality | No swelling | 5/5 is health and living |
| | Repeated inoculation with single dose | 5 pigs | 25 | Neck muscle injection | 2 ml/pig | 2 | No abnormality | No swelling | 5/5 is health and living |
| | Control | 5 pigs | 25 | Neck muscle injection | 2 ml/pig | 2 | No abnormality | No swelling | 5/5 is health and living |
| Replacement gilts | Primary inoculation with single dose | 5 pigs | 180 | Neck muscle injection | 2 ml/pig | 1 | No abnormality | No swelling | 5/5 is health and living |
| | Primary inoculation with super times of dose | 5 pigs | 180 | Neck muscle injection | 4 ml/pig | 1 | No abnormality | No swelling | 5/5 is health and living |
| | Repeated inoculation with single dose | 5 pigs | 180 | Neck muscle injection | 2 ml/pig | 2 | No abnormality | No swelling | 5/5 is health and living |
| | Control | 5 pigs | 180 | Neck muscle injection | 2 ml/pig | 2 | No abnormality | No swelling | 5/5 is health and living |

TABLE 12

Result of safety test of pregnant sows

| Animal | Inoculation way | Quantity | Inoculation route | Injection dose | Times of immunization | Observation items: General reaction | Observation items: Injection site | Result |
|---|---|---|---|---|---|---|---|---|
| Pregnant sows | Primary inoculation with single dose | 5 pigs | Neck muscle injection | 2 ml/pig | 1 | No abnormality | No swelling | 5/5 of sows are healthy and living; one sow is accidentally aborted due to the mechanical stimulation and others are delivered normally; and the borne piglets are normal |
| | Primary inoculation with super times of dose | 5 pigs | Neck muscle injection | 4 ml/pig | 1 | No abnormality | No swelling | 5/5 of sows are healthy and living, and delivered normally; and the borne piglets are normal |
| | Repeated inoculation with single dose | 5 pigs | Neck muscle injection | 2 ml/pig | 2 | No abnormality | No swelling | 5/5 of sows is healthy and living, and delivered normally; and the borne piglets are normal |
| | Control | 5 pigs | Neck muscle injection | 2 ml/pig | 2 | No abnormality | No swelling | 5/5 of sows is healthy and living, and delivered normally; and the borne piglets are normal |

We claim:

1. A vaccine of porcine pseudorabies virus (PRV), comprising an adjuvant and a virus liquid containing an inactivated porcine pseudorabies virus PRV-YF strain; wherein the PRV-YF strain is isolated from tonsils and brain tissues of pathogenetic piglets; the preservation name is porcine pseudorabies virus PRV-YF strain; the preservation organization is China Center for Type Culture Collection (CCTCC); the preservation date is Jan. 21, 2015; and the preservation number is CCTCC No. V201502.

2. A preparation method for the vaccine of the porcine pseudorabies virus according to claim 1, comprising the following steps:

1) culturing the porcine pseudorabies virus PRV-YF strain to obtain a virus liquid;

2) adding an inactivator in the virus liquid for inactivating the virus; and then, adding a terminator for terminating inactivation to obtain an inactivated virus liquid of the PRV-YF strain; and 3) preparing a water phase and an oil phase and emulsifying to obtain the vaccine of the porcine pseudorabies virus.

3. The preparation method according to claim 2, characterized in that: the virus content of the virus liquid prepared in Step 1) is not less than $10^{7.0}$ $TCID_{50}$/ml.

4. The preparation method according to claim 2, characterized in that: the inactivator described in Step 2) is pyrrole; and weighing by w/v, the pyrrole added in the virus liquid accounts for 0.1% to 1% of the total amount of the virus liquid.

5. The preparation method according to claim 2, characterized in that: the inactivation time is 12 to 60 h; and the inactivation temperature is 37° C.

6. The preparation method according to claim 2, characterized in that: the terminator described in Step 2) is sodium thiosulfate; and weighing by w/v, the sodium thiosulfate added in the virus liquid accounts for 0.1% to 5% of the total amount of the virus liquid.

7. The preparation method according to claim 2, characterized in that: weighing by w/v, the sodium thiosulfate added in the virus liquid accounts for 0.5% to 5% of the total amount of the virus liquid.

8. The preparation method according to claim 2, characterized in that: Step 3) comprises the following steps:

A. Preparation of water phase: taking the inactivated virus liquid of the PRV-YP strain prepared in Step 2) and adding the same into Span-80 with the final concentration of 0.75%, mixing while adding until Span-80 is thoroughly dissolved, thereby generating the water phase;

B. Preparation of oil phase: taking 141.75 parts of white oil, adding 7.5 parts of Span-80, fully mixing, sterilizing for 30 min at 121° C., cooling to room temperature for standby, thereby generating the oil phase;

C. Emulsifying the oil phase and the water phase by 1.5:1; adding the water phase into the oil phase slowly, shearing after homogenizing for 1-3 min, thereby generating a homogeneous emulsion.

* * * * *

SEQUENCE LISTING

<160> NUMBER OF SEQ ID NOS: 2

<210> SEQ ID NO 1
<211> LENGTH: 1742
<212> TYPE: DNA
<213> ORGANISM: Artificial Sequence
<220> FEATURE:
<223> OTHER INFORMATION: gE whole-genome sequence

<400> SEQUENCE: 1
atgcggccct ttctgctgcg cgccgcgcag ctcctggcgc tgctggccct ggcgctctcc 60
accgaggccc cgagcctctc cgccgagacg accccgggcc ccgtcaccga ggtcccgagt 120
ccctcggccg aggtctggga cgacctctcc accgaggccg acgacgatga cctcaacggc 180
gacctcgacg gcgacgaccg ccgcgcgggc ttcggctcgg ccctcgcatc cctgagggag 240
gcgcccccgg cccatctggt gaacgtgtcc gagggcgcca acttcaccct cgacgcgcgc 300
ggcgacggcg ccgtgctggc cgggatctgg acgttcctgc ccgtccgcgg ctgcgacgcc 360
gtgtcggtga ccacggtgtg cttcgagacc gcgtgccacc cggacctggt gctgggccgc 420
gcctgcgtcc ccgaggcccc ggagatgggc atcggcgact acctgccgcc cgaggtgccg 480
cggctccggc gcgagccgcc catcgtcacc ccggagcggt ggtcgccgca cctgagcgtc 540
ctgcgggcca cgcccaacga cacgggcctc tacacgctgc acgacgcctc ggggccgcgg 600
gccgtgttct ttgtggcggt gggcgaccgg ccgcccgcgc cggcggaccc ggtgggcccc 660
gcgcgccacg agccccgctt ccacgcgctc ggcttccact cgcagctctt ctcgcccggg 720
gacacgttcg acctgatgcc gcggggtggt ctcggacatg ggcgactcgc gcgagaactt 780
ttaccgccac gctggactgg tactacgcgc gcgcgccccc gcggtgcctg ctgtactacg 840
tgtacgagcc ctgcatctac cacccgcgcg cgcccgagtg cctgcgcccg gtggacccgg 900
cgtgcagctt cacctcgccg gcgcgcgcgc ggctggtggc gcgccgcgcg tacgcctcgt 960
gcagcccgct gctcggggac cggtggctga ccgcctgccc cttcgacgcc ttcggcgagg 1020
aggtgcacac gaacgccacc gcggacgagt cggggctgta cgtgctcgtg atgacccaca 1080
acggccacgt cgccacctgg gactacacgc tcgtcgccac cgcggccgag tacgtcacgg 1140
tcatcaagga gctgacggcc acggcccggg ccccgggcac cccgtggggc cccggcggcg 1200
gcgacgacgc gatctacgtg gacggcgtca cgacgccggc gccgcccgcg cgcccgtgga 1260
acccgtacgg ccggacgacg cccgggcggc tgtttgtgct ggcgctgggc tccttcgtga 1320
tgacgtgcgt cgtcgggggg gccatctggc tctgcgtgct gtgctcccgg cgccgggcgg 1380
cctcgcggcc gttccgggtg ccgacgcggg cgcggacgca catgctctct ccggtgtaca 1440
ccagcctgcc cacgcacgag gactactacg acggcgacga cgacgacgac gaggaggcgg 1500
gcgtcatccg ccggcggccc gcctccccca gcggagacag cggctacgag gggccgtacg 1560
cgagcctgga ccccgaggac gagttcagca gcgacgagga cgacgggctg tacgtgcgcc 1620
ccgaggaggc gccccgctcc ggcttcgacg tctggttccg cgatccggag aaaccggaag 1680
tgacgaatgg acccaactat ggcgtgaccg ccaaccgcct gttgaatgcc cgccccgctt 1740
aa 1742

<210> SEQ ID NO 2
<211> LENGTH: 1501
<212> TYPE: DNA
<213> ORGANISM: Artificial Sequence
<220> FEATURE:
<223> OTHER INFORMATION: gG whole-genome sequence -continued

```
<400> SEQUENCE: 2

atgaagtggg caacgtggat cctcgccctc gggctcctcg tggtccgcac cgtcgtggcc     60

agagaggccc ctcgggagct ctgctacggc caccccgtcc acgacgaccg gcggcccgtc    120

gggcccgcga ccgacgccca gcccgtgaac ccgctcgccc ccgccaacgc caccgggacg    180

gactactctc gcggctgcga gatgcgcctc ctggacccgc ctctcgatgt ctcgtcccgc    240

tccccggacc ccgtcaacgt gaccgtcgcc tggttctttg acggcggcca ctgcaaggtg    300

cccctcgtcc accgcgagta ctacggctgc cccggggacg ccatgccctc cgtcgagacg    360

tgcaccggcg ggtactcgta cacccgcacg cgcatcgaca ccctgatgga gtacgccctc    420

gtgaacgcca gcctcgtgct gcagcccggg ctgtacgacg ccggcctgta catcgtcgtg    480

ctcgtctttg gcgacgacgc ctacctcggc accgtctccc tgtcggtgga ggccaacctg    540

gactacccct gcggcatgaa gcacgggctc acgatcaccc gccccggggc caccctcccg    600

cccatcgccc ccacggccgg cgaccaccag cgctggcgcg ggtgcttccc ctcgaccgac    660

gagggcgcct gggagaacgt gaccgccgcc gagaagggcc tgtccgacga ctacgccgac    720

tactacgacg tgcacatctt ccgcctggag tctgacgacg aggtcgtcca cggcgatgcc    780

cccgaggccc ccgagggcga ggaggtgacc gaggaggagg ccgagctgac ctccagcgac    840

ctcgacaaca tcgagatcga ggtcgtgggc tcgctcgccg ctcccgtcga gggcgccggc    900

gacggcgagg aggggcacgg ggacgaggag gacgaggagc tgacctccag cgacctcgac    960

aacatcgaga tcgagggtcg tgggctcgcc cgcggccgcc cgcttcttcg ccgcctccac   1020

caccccccgc gcccccaccc gcgcggccga gatcacgacc atgaccacgg tcaccaccgt   1080

gcggacgacc gaggacccca gcggcatcac cgactgccgc cggagcgact tcgtctcgcc   1140

ctctgacatc ttcgtgaccc ccaccggcag ccccgccctg ctcctgggct tcctgggcag   1200

cgcgctcgcc tcgcgccccc tgcacctgac ggccggggag acggcccagc acgtgcgcga   1260

ggcccagcag aagagccgcc acgtccgctc cctcggcggc ctccagttct cggtcgagac   1320

cgagaccacc aacaccacca ccacccagac gggcctgtcg ggcgacatcc gcacctcgat   1380

ctacatctgc gtcgccctcg ccggcctggt cgtcgtgggc atcgtcatca tgtgcctcca   1440

catggcgatc atcagggccc gggcccggaa cgacggctac cgccacgtgg cctccgcctg   1500

a                                                                   1501
```